United States Patent [19]

Yamaguchi et al.

[11] 4,248,804

[45] Feb. 3, 1981

[54] PROCESS FOR THE PREPARATION OF 2,2'-BIS[4-(1,1,3,3-TETRAMETHYLBUTYL)-PHENOL]SULFIDE

[75] Inventors: Akihiro Yamaguchi; Tadashi Kobayashi, both of Yokohama; Keisaburo Yamaguchi, Kawasaki; Hisamichi Murakami, Yokohama, all of Japan

[73] Assignee: Mitsui Toatsu Chemicals, Incorporated, Tokyo, Japan

[21] Appl. No.: 70,614

[22] Filed: Aug. 29, 1979

[30] Foreign Application Priority Data

Sep. 7, 1978 [JP] Japan ................................ 53-109136
Sep. 18, 1978 [JP] Japan ................................ 53-113651

[51] Int. Cl.³ ........................................ C07C 149/36
[52] U.S. Cl. ........................................ 568/47
[58] Field of Search ........................ 260/609 F

[56] References Cited

U.S. PATENT DOCUMENTS

2,971,968  2/1961  Nicholson, Jr. et al. ..... 260/45.75 N
3,726,928  4/1973  Fuchsman ....................... 260/609 F

FOREIGN PATENT DOCUMENTS

1275067  8/1968  Fed. Rep. of Germany.

OTHER PUBLICATIONS

V. Tishkova et al., Chem. Abstracts, vol. 60: 9075d (1964).

*Primary Examiner*—Donald G. Daus
*Assistant Examiner*—M. C. Eakin

[57] ABSTRACT

2,2'-bis[4-(1,1,3,3-tetramethylbutyl)phenol]sulfide is prepared by suspending 4-(1,1,3,3-tetramethylbutyl)-phenol in an organic solvent, reacting it with sulfur dichloride or sulfur monochloride at a temperature of from $-10°$ to $40°$ C., and isolating the precipitate so formed.

18 Claims, No Drawings

PROCESS FOR THE PREPARATION OF 2,2'-BIS[4-(1,1,3,3-TETRAMETHYLBUTYL)-PHENOL]SULFIDE

BACKGROUND OF THE INVENTION (1) Field of the Invention

This invention relates to an improved process for the preparation of 2,2'-bis[4-(1,1,3,3-tetramethylbutyl)phenol]sulfide which is useful as a light stabilizer, polyolefin modifier, lubricating oil additive, and an intermediate for the manufacture thereof.

(2) Description of the Prior Art

Generally, 2,2'-bis(4-substituted phenol)monosulfides are prepared by reaction of a corresponding 4-substituted phenol with sulfur dichloride. However, further sulfidation in the 6-position of the resulting monosulfide proceeds concurrently to form polynuclear byproducts. Moreover, sulfur dichloride takes part in the chemical equilibrium represented by the equation

$$2SCl_2 \rightleftarrows S_2Cl_2 + Cl_2 \qquad (1)$$

This leads to a more complicated reaction in which disulfides and other polysulfides are formed as by-products. In many cases, therefore, the end product is undesirably obtained in resinous form and in low yield.

Likewise, 2,2'-bis[4-(1,1,3,3-tetramethylbutyl)phenol]sulfide to which this invention is directed is conventionally prepared by reaction of 4-(1,1,3,3-tetramethylbutyl)phenol with sulfur dichloride, and a number of processes based on this principle are well known. One exemplary process comprises the steps of effecting the reaction in carbon tetrachloride at a temperature of 7° C., diluting the reaction mixture with a large amount of petroleum ether, and then isolating the crystals so precipitated (U.S. Pat. No. 2,971,968 (1961); Chemical Abstracts, Vol. 55, 14385 (1961). Another exemplary process, which has more recently been proposed, comprises the steps of effecting the reaction in a hydrocarbon solvent at a temperature of from 50° to 63° C., cooling the reaction mixture, and then isolating the precipitate so formed (German Pat. No. 1,275,067 (1968). However, these processes adopt the conventional idea of dissolving 4-(1,1,3,3-tetramethylbutyl)phenol in a solvent and then reacting it with sulfur dichloride, and the yield of the end product is as low as 40% for the former process and 17–40% for the latter one. Moreover, these processes require an additional step for the crystallization of the end product by diluting or cooling the reaction mixture. For these reasons, these processes cannot be regarded as economical and suitable for industrial purposes.

On the other hand, it is well known that 4-(1,1,3,3-tetramethylbutyl)phenol reacts with sulfur monochloride ($S_2Cl_2$) to form the corresponding disulfide. Specifically, a quantitative yield of 2,2'-bis[4-(1,1,3,3-tetramethylbutyl)phenol]disulfide can be obtained by heating both reactants in the toluene solvent (Tr. Mosk. Inst. Neftekim Gaz. Prom., No. 44, P. 105 (1963)).

SUMMARY OF THE INVENTION

It is an object of this invention to provide an improved process for the preparation of 2,2'-bis[4-(1,1,3,3-tetramethylbutyl)phenol]sulfide by which a good yield of highly pure product can be obtained with great industrial advantages.

This object can readily be accomplished by a process which comprises the steps of suspending 4-(1,1,3,3-tetramethylbutyl)phenol in an organic solvent and then reacting it with sulfur dichloride or sulfur monochloride at a temperature of from −10° to 40° C. The resulting crystals of 2,2'-bis[4-(1,1,3,3-tetramethylbutyl)phenol]sulfide are subsequently isolated from the solvent.

In accordance with this invention, it has been unexpectedly found that 4-(1,1,3,3-tetramethylbutyl)phenol need not be dissolved in an organic solvent, but rather must be suspended therein for the purpose of achieving a high yield of the isolated product. More specifically, it is of great advantage to suspend the phenol totally or partially in an organic solvent and then react it with sulfur dichloride or sulfur monochloride.

Moreover, the resulting product precipitates spontaneously from the reaction mixture. Accordingly, the monosulfide in an industrially pure form can be directly isolated by filtration of the reaction mixture, leaving very small amounts of unreacted phenol and by-products in the solvent.

Another advantage of this invention is that, since the mother liquor from which the product has been isolated contains only very small amounts of unreacted phenol and by-products, it can be cyclically used without any adverse effect on the properties of the newly formed product, or 2,2'-bis[4-(1,1,3,3-tetramethylbutyl)phenol]sulfide. What is more, if the product is sparingly soluble in the mother liquor, the yield of the isolated product is further enhanced by recycling the mother liquor. This not only allows a saving of solvent and hence a reduction in cost, but also substantially eliminates the problems concerning environmental pollution, thus bringing about great improvements on the prior art from an industrial point of view.

As stated before, it is well known that a disulfide is obtained by reacting 4-(1,1,3,3-tetramethylbutyl)phenol with sulfur monochloride. In accordance with this invention, however, it has been unexpectedly found that the main product obtained by suspending 4-(1,1,3,3-tetramethylbutyl)phenol in an organic solvent and then reacting it with sulfur monochloride at a temperature of from −10° to 40° C. is 2,2-bis[4-(1,1,3,3-tetramethylbutyl)phenol]sulfide, and not the aforesaid disulfide.

DETAILED DESCRIPTION OF THE PREFERRED EMBODIMENTS

The organic solvent used in the process of the invention can by any of the common organic solvents in which 4-(1,1,3,3-tetramethylbutyl)phenol is totally or partially suspended at temperatures ranging from −10° to 40° C. They include, for example, aliphatic hydrocarbons such as, butane, pentane, hexane, isohexane, heptane, isoheptane, octane, isooctane, etc.; and alicyclic hydrocarbons such as cyclopentane, cyclohexane, methylcyclohexane, etc. Halogenated hydrocarbons, aromatic hydrocarbons, ethers, and esters can also be used, as long as they are inert to sulfur monochloride. However, the solubility of 4-(1,1,3,3-tetramethylbutyl)phenol in these compounds may be so high that the phenol is dissolved therein at temperatures ranging from −10° to 40° C. For this reason, these compounds are desirably used by mixing them with the aforesaid aliphatic or alicyclic hydrocarbons in such a proportion that the phenol is totally or partially suspended in the mixed solvent at temperatures ranging from −10° to 40° C. The amount of solvent used is generally from 0.5 to 10 parts by volume and preferably from about 2 to 5 parts by volume per part by weight of 4-(1,1,3,3-tetramethylbutyl)phenol.

In the process of the invention, it is preferable to react every 2 moles of 4-(1,1,3,3-tetramethylbutyl)phenol with 1 mole of sulfur dichloride or sulfur monochloride. However, the amount of sulfur dichloride or sulfur monochloride used may vary from 0.8 to 1.5 moles.

In the process of the invention, the reaction proceeds in the absence of catalyst. However, the use of a Lewis acid as catalyst further promotes the reaction and enhances the yield. Specific examples of the Lewis acid include aluminum chloride, zinc chloride, stannic chloride, and ferric chloride. Among these compounds, zinc chloride is particularly preferred. The catalyst may be used in a very small but catalytically effective amount which is generally from 0.001 to 0.1 mole per mole of sulfur dichloride or sulfur monochloride.

In the process of the invention, it is necessary to effect the reaction at a temperature of from $-10°$ to $40°$ C. If the reaction temperature is lower than $-10°$ C., the reaction time is prolonged excessively, while if it is higher than $40°$ C., the phenol tends to dissolve in the solvent and, therefore, the yield of the product is reduced extremely. The preferred temperature range is from $-10°$ to $20°$ C. If a temperature within this range is used, the reaction is nearly completed from 1 to 5 hours after the addition of sulfur dichloride or sulfur monochloride.

In carrying out the process of the invention, the starting materials (namely, 4-(1,1,3,3-tetramethylbutyl)phenol and sulfur dichloride or sulfur monochloride), solvent and optionally used catalyst may be charged in any desired order and by any desired manner. For the purpose intended by this invention, however, it is preferable to add sulfur dichloride or sulfur monochloride drop by drop to a suspension of the phenol in an organic solvent. The rate of addition is preferably controlled so that the hydrogen chloride gas resulting from the reaction may be evolved continuously. If necessary, a mixture of sulfur dichloride or sulfur monochloride and an organic solvent may be added to the suspension. In general, 4-(1,1,3,3-tetramethylbutyl)phenol is suspended in the above-defined solvent and, if desired, a catalytically effective amount of a Lewis acid is added thereto. While this suspension is kept at a temperature of from $-10°$ to $40°$ C., sulfur dichloride or sulfur monochloride is added thereto drop by drop. After completion of the addition, the resulting reaction mixture is stirred at that temperature for a period of from 1 to 5 hours. The precipitate so formed is separated by filtration, washed first with a small amount of the above-defined solvent and then with water, and dried.

Whether the second reactant is sulfur dichloride or sulfur monochloride, the yield of the product, or 2,2'-bis[4-(1,1,3,3-tetramethylbutyl)phenol]sulfide, is 60% or higher and particularly 80% or higher in the case of sulfur dichloride. The product has a satisfactorily high purity of from 95 to 98%, and requires no additional purification step. Thus, it can be directly used as a light stabilizer, modifier, lubricating oil additive, and an intermediate for the manufacture thereof.

The present invention is further illustrated by the following examples.

EXAMPLE 1

In 150 ml of n-hexane was suspended 41.2 g (0.2 mole) of 4-(1,1,3,3-tetramethylbutyl)phenol. While this suspension was kept at a temperature of $0°-10°$ C., 11.3 g (0.11 mole) of sulfur dichloride was added thereto drop by drop over a period of about one hour. Thereafter, the resulting reaction mixture was stirred at that temperature for an additional hour. The precipitate so formed was separated by filtration, washed first with 30 ml of n-hexane and then with water, and dried to obtain a yield of 40.4 g (91.3%) of white product melting at $133°-135°$ C. This product was found to be 2,2'-bis[4-(1,1,3,3-tetramethylbutyl)phenol]sulfide having a purity of 96.5%. Then, it was further purified by recrystallization from cyclohexane and the resulting pure product consisted of white needle-like crystals melting at $135°-136°$ C. The results of elemental analysis were as follows:

|  | C (%) | H (%) | S (%) |
|---|---|---|---|
| Calculated Values | 75.97 | 9.56 | 7.24 |
| Found Values | 76.05 | 9.63 | 7.23 |

EXAMPLE 2

The procedure of Example 1 was repeated except that 0.5 g of zinc chloride was added to the reaction mixture. As a result, a yield of 42.0 g (94.5%) of product melting at $133°-135°$ C. was obtained. This product was found to be 2,2'-bis[4-(1,1,3,3-tetramethylbutyl)phenol]sulfide having a purity of 96.4%.

EXAMPLE 3

The mother liquor and washings left behind in Example 1 were combined and a 150 ml portion was reused as a solvent. That is, 41.2 g (0.2 mole) of 4-(1,1,3,3-tetramethylbutyl)phenol was suspended in this solvent and the procedure of Example 1 was repeated to obtain a yield of 42.0 g (95.2%) of product melting at $133°-135°$ C. This product was found to be 2,2'-bis[4-(1,1,3,3-tetramethylbutyl)phenol]sulfide having a purity of 96.5%.

EXAMPLE 4

The mother liquor and washings left behind in Example 3 were combined and a 150 ml portion was reused as a solvent. The procedure of Example 3 was repeated to obtain a yield of 42.4 g (96.0%) of product melting at $133°-135°$ C. This product was found to be 2,2'-bis[4-(1,1,3,3-tetramethylbutyl)phenol]sulfide having a purity of 96.4%.

EXAMPLE 5

The procedure of Example 1 was repeated except that the n-hexane (150 ml) was replaced by 120 ml of cyclohexane. As a result, a yield of 39.1 g (88.5%) of product melting at $133°-135°$ C. was obtained. This product was found to be 2,2'-bis[4-(1,1,3,3-tetramethylbutyl)phenol]sulfide having a purity of 97.5%.

EXAMPLE 6

The procedure of Example 2 was repeated except that the n-hexane (150 ml) was replaced by a mixture of 30 ml of carbon tetrachloride and 120 ml of n-hexane. As a result, a yield of 40.9 g (92.5%) of product melting at $133°-135°$ C. was obtained. This product was found to be 2,2'-bis[4-(1,1,3,3-tetramethylbutyl)phenol]sulfide having a purity of 97.3%.

EXAMPLE 7

The procedure of Example 2 was repeated except that the n-hexane (150 ml) was replaced by a mixture of 40 ml of benzene and 110 ml of n-hexane and the zinc chloride (0.5 g) was replaced by 0.5 g of stannic chloride. As a result, a yield of 40.0 g (90.5%) of product melting 133°–135° C. was obtained. This product was found to be 2,2'-bis[4-(1,1,3,3-tetramethylbutyl)phenol]-sulfide having a purity of 97.0%.

EXAMPLE 8

In n-hexane was suspended 41.2 g (0.2 mole) of 4-(1,1,3,3-tetramethylbutyl)phenol. While this suspension was kept at a temperature of 35°–40° C., 11.3 g (0.11 mole) of sulfur dichloride was added thereto drop by drop over a period of about one hour. Thereafter, the resulting reaction mixture was stirred at that temperature for an additional hour and then allowed to cool to room temperature. The precipitate so formed was separated by filtration, washed first with 30 ml of n-hexane and then with water, and dried to obtain a yield of 36.9 g (83.5%) of product melting at 132°–135° C. This product was found to be 2,2'-bis[4-(1,1,3,3-tetramethylbutyl)phenol]sulfide having a purity of 95.0%.

EXAMPLE 9

In 150 ml of n-hexane was suspended 41.2 g (0.2 mole) of 4-(1,1,3,3-tetramethylbutyl)phenol. While this suspension was kept at a temperature of 0°–10° C., 14.8 g (0.11 mole) of sulfur monochloride was added thereto drop by drop over a period of about one hour. Thereafter, the resulting reaction mixture was stirred at that temperature for an additional hour. The precipitate so formed was separated by filtration, washed first with 30 ml of n-hexane and then with water, and dried to obtain a yield of 30.3 g (68.5%) of white product melting at 133°–135° C. This product was found to be 2,2'-bis[4-(1,1,3,3-tetramethylbutyl)phenol]sulfide having a purity of 96.0%.

EXAMPLE 10

The procedure of Example 9 was repeated except that 0.5 g of zinc chloride was added to the reaction mixture. As a result, a yield of 32.5 g (73.5%) of product melting at 133°–135° C. was obtained. This product was found to be 2,2'-bis[4-(1,1,3,3-tetramethylbutyl)phenol]-sulfide having a purity of 96.0%.

EXAMPLE 11

The procedure of Example 9 was repeated except that the n-hexane (150 ml) was replaced by 120 ml of cyclohexane. As a result, a yield of 29.0 g (65.6%) of product melting at 133°–135° C. was obtained. This product was found to be 2,2'-bis[4-(1,1,3,3-tetramethylbutyl)phenol]sulfide having a purity of 97.0%.

EXAMPLE 12

The procedure of Example 10 was repeated except that the n-hexane (150 ml) was replaced by a mixture of 30 ml of carbon tetrachloride and 120 ml of n-hexane. As a result, a yield of 31.1 g (70.4%) of product melting at 133°–135° C. was obtained. This product was found to be 2,2'-bis[4-(1,1,3,3-tetramethylbutyl)phenol]sulfide having a purity of 96.5%.

EXAMPLE 13

The procedure of Example 10 was repeated except that the n-hexane (150 ml) was replaced by a mixture of 40 ml of benzene and 110 ml of n-hexane and the zinc chloride (0.5 g) was replaced by 0.5 g of stannic chloride. As a result, a yield 30.8 g (69.7%) of product melting at 133°–135° C. was obtained. This product was found to be 2,2'-bis[4-(1,1,3,3-tetramethylbutyl)phenol]-sulfide having a purity of 96.2%.

EXAMPLE 14

In 150 ml of n-hexane was suspended 41.2 g (0.2 mole) of 4-(1,1,3,3-tetramethylbutyl)phenol. While this suspension was kept at a temperature of 35°–40° C., 14.8 g (0.11 mole) of sulfur monochloride was added thereto drop by drop over a period of about one hour. Thereafter, the resulting reaction mixture was stirred at that temperature for an additional hour and then allowed to cool to room temperature. The precipitate so formed was separated by filtration, washed first with 30 ml of n-hexane and then with water, and dried to obtain a yield of 25.8 g (58.5%) of product melting at 132°–135° C. This product was found to be 2,2'-bis[4-(1,1,3,3-tetramethylbutyl)phenol]sulfide having a purity of 95.5%.

What is claimed is:

1. In a process for the preparation of 2,2'-bis-[4-(1,1,3,3-tetramethylbutyl)phenol]sulfide by the reaction of 4-(1,1,3,3-tetramethylbutyl)phenol with a sulfidation agent selected from the group consisting of sulfur dichloride and sulfur monochloride, the improvement which comprises mixing the said 4-(1,1,3,3-tetramethylbutyl)phenol at a temperature of from −10° to 40° C. with an organic solvent selected from the group consisting of aliphatic hydrocarbons, alicyclic hydrocarbons and mixtures of aliphatic hydrocarbons with halogenated hydrocarbons or aromatic hydrocarbons, said solvent being in an amount insufficient for totally dissolving the 4-(1,1,3,3-tetramethylbutyl)phenol, thereby forming a suspension of the 4-(1,1,3,3-tetramethylbutyl)phenol in the organic solvent, and subjecting the resulting suspension to the reaction with the sulfidation agent at a temperature of from −10° to 40° C.

2. A process as claimed in claim 1 wherein the reaction is effected in the presence of a Lewis acid catalyst.

3. A process as claimed in claim 2 wherein the Lewis acid catalyst is aluminum chloride, zinc chloride, stannic chloride, or ferric chloride.

4. A process as claimed in claim 2 wherein the Lewis acid catalyst is used in an amount of from 0.001 to 0.1 mole per mole of the sulfidation agent.

5. A process as claimed in claim 2 wherein the sulfidation agent is used in a proportion of from 0.8 to 1.5 moles for every 2 moles of the 4-(1,1,3,3-tetramethylbutyl)phenol.

6. A process as claimed in claim 1 wherein the organic solvent is a straight-chain or branched aliphatic hydrocarbon having from 4 to 8 carbon atoms.

7. A process as claimed in claim 1 wherein the organic solvent is cyclopentane, cyclohexane, or an alkyl-substituted derivative thereof.

8. A process as claimed in claim 1 wherein the organic solvent is used in an amount of from 0.5 to 10 parts by volume per part by weight of the 4-(1,1,3,3-tetramethylbutyl)phenol.

9. A process as claimed in claim 8 wherein the reaction is effected at a temperature of from −10° to 20° C.

10. A process for the preparation of 2,2'-bis[4-(1,1,2,2-tetramethylbutyl)phenol]sulfide which comprises the steps of mixing 4-(1,1,3,3-tetramethylbutyl)phenol at a temperature of from −10° to 40° C. with an aliphatic or alicyclic hydrocarbon in an amount of from 0.5 to 10 parts by volume per part by weight of the 4-(1,1,3,3-tetramethylbutyl)-phenol to form a suspension of the 4-(1,1,3,3-tetramethylbutyl)-phenol in the hydrocarbon; reacting the 4-(1,1,3,3-tetramethylbutyl)phenol with sulfur dichloride in the presence of a Lewis acid at a temperature of from −10° to 40° C.; and then isolating the resulting crystals of 2,2'-bis[4-1,1,3,3-tetramethylbutyl)-phenol]sulfide.

11. A process for the preparation of 2,2'-bis[4-(1,1,3,3-tetramethylbutyl)phenol]sulfide which comprises the steps of mixing 4-(1,1,3,3-tetramethylbutyl)phenol at a temperature of from −10° to 40° C. with an aliphatic or alicyclic hydrocarbon in an amount of from 0.5 to 10 parts by volume per part by weight of the 4-(1,1,3,3-tetramethylbutyl)-phenol to form a suspension of the 4-(1,1,3,3-tetramethylbutyl)-phenol in the hydrocarbon; reacting the 4-(1,1,3,3-tetramethylbutyl)phenol with sulfur monochloride in the presence of a Lewis acid at temperature of from −10° to 40° C.; and isolating the resulting crystals of 2,2'-bis[4-(1,1,3,3-tetramethylbutyl)phenol]-sulfide.

12. A process as claimed in claim 10 wherein the Lewis acid is aluminum chloride, zinc chloride, stannic chloride, or ferric chloride.

13. A process as claimed in claim 11 wherein the Lewis acid is aluminum chloride, zinc chloride, stannic chloride, or ferric chloride.

14. In a process for the preparation of 2,2'-bis[4-(1,1,3,3-tetramethylbutyl)phenol]sulfide by the reaction of 4-(1,1,3,3-tetramethylbutyl)phenol with a sulfidation agent selected from the group consisting of sulfur dichloride and sulfur monochloride, the improvement which comprises mixing the 4-(1,1,3,3-tetramethylbutyl)phenol at a temperature of from −10° to 40° C. with an organic solvent selected from the group consisting of aliphatic hydrocarbons, alicyclic hydrocarbons and mixtures of aliphatic hydrocarbons with halogenated hydrocarbons or aromatic hydrocarbons, said solvent being in an amount of from 0.5 to 10 parts by volume per part by weight of the 4-(1,1,3,3-tetramethylbutyl)phenol to form a suspension of the 4-(1,1,3,3-tetramethylbutyl) phenol in the hydrocarbon, and subjecting the suspension to the reaction with the sulfidation agent at a temperature of from −10° to 40° C.

15. A process as claimed in claim 14, wherein the reaction is effected in the presence of a Lewis acid catalyst selected from the group consisting of aluminum chloride, zinc chloride, stannic chloride, or ferric chloride.

16. A process as claimed in claim 14, wherein the 4-(1,1,3,3-tetramethylbutyl)phenol is mixed at a temperature of from −10° to 20° C. with an aliphatic or alicyclic hydrocarbon in an amount of from 2 to 5 parts by volume of hydrocarbon per part by weight of 4-(1,1,3,3-tetramethylbutyl)phenol.

17. A process as claimed in claim 10 wherein the 4-(1,1,3,3-tetramethylbutyl)phenol is mixed at a temperature of from −10° to 20° C. with the hydrocarbon in an amount of from 2 to 5 parts by volume of hydrocarbon per part by weight of 4-(1,1,3,3-tetramethylbutyl)phenol.

18. A process as claimed in claim 11, wherein the 4-(1,1,3,3-tetramethylbutyl)phenol is mixed at a temperature of from −10° to 20° C. with the hydrocarbon in an amount of from 2 to 5 parts by volume of hydrocarbon per part by weight of 4-(1,1,3,3-tetramethylbutyl)phenol.

* * * * *